(12) United States Patent
Kim et al.

(10) Patent No.: US 8,193,345 B2
(45) Date of Patent: Jun. 5, 2012

(54) PURIFICATION METHOD OF LACTONE COMPOUNDS CONTAINING UNSATURATED ALKYL GROUP BY EXTRACTION WITH SILVER ION SOLUTION

(75) Inventors: Jae Jong Kim, Daejeon (KR); Si Kyu Lim, Daegu (KR); Mi Ok Lee, Deajeon (KR); Sang Myoun Lim, Daejeon (KR); Bo-mi Lee, Nonsan-si (KR); Dong Hwan Kim, Daejeon (KR); Keum Soon Lee, Daejeon (KR); Jeoung Hyun Ryu, Cheongju-si (KR)

(73) Assignee: Genotech Corp., Daejeon (KR)

( * ) Notice: Subject to any disclaimer, the term of this patent is extended or adjusted under 35 U.S.C. 154(b) by 0 days.

(21) Appl. No.: 13/051,948

(22) Filed: Mar. 18, 2011

(65) Prior Publication Data

US 2011/0172413 A1   Jul. 14, 2011

Related U.S. Application Data

(63) Continuation of application No. PCT/KR2009/004325, filed on Aug. 3, 2009.

(30) Foreign Application Priority Data

Sep. 18, 2008   (KR) .................. 10-2008-0091523

(51) Int. Cl.
*C07D 498/16* (2006.01)
(52) U.S. Cl. ..................................... 540/456
(58) Field of Classification Search ............. 540/456
See application file for complete search history.

(56) References Cited

U.S. PATENT DOCUMENTS

| 4,894,366 | A | 1/1990 | Okuhara et al. |
| 5,624,842 | A | 4/1997 | Okuhara et al. |
| 6,492,513 | B1 | 12/2002 | Nishihara et al. |
| 6,576,135 | B1 | 6/2003 | Higaki et al. |
| 6,881,341 | B2 | 4/2005 | Higaki et al. |
| 7,473,366 | B2 * | 1/2009 | Patil et al. ............ 210/635 |
| 2008/0000834 | A1 | 1/2008 | Cvak et al. |

FOREIGN PATENT DOCUMENTS

| JP | 06247954 A | 9/1994 |
| JP | 2001048819 A | 2/2001 |
| WO | 0071546 A1 | 11/2000 |
| WO | 0118007 A2 | 3/2001 |
| WO | 2005054253 A1 | 6/2005 |
| WO | 2005098011 A1 | 10/2005 |

OTHER PUBLICATIONS

Kino, T. et al., FK-506, A novel immunosuppressant isolated from a streptomyces, I. Fermentation, isolation, and physico-chemical and biological characteristics, The Journal of Antibiotics, 1987, vol. XL, No. 9, pp. 1249-1255.
Kino, T. et al., FK-506, A novel immunosuppressant isolated from a streptomyces, II. Immunosuppressive effect of FK-506 in vitro, The Journal of Antibiotics, 1987, vol. XL, No. 9, pp. 1256-1265.
Vonach, B. et al., High-performance liquid chromatography with Ag+ complexation in the mobile phase, Journal of Chromatography, 1978, vol. 149, pp. 417-430.
Catalog of Astellas Pharma. Inc., ( 2009).
International Search Report dated Jan. 11, 2010, issued for PCT/KR2009/004325.
Muramatsu, Hideyuki et al., Phylogenetic analysis of immunosuppressant FK506-producing streptomycete strains, Actinomycetologica, 2005, vol. 19, No. 2, pp. 33-39.

* cited by examiner

*Primary Examiner* — Bruck Kifle
(74) *Attorney, Agent, or Firm* — Knobbe, Martens, Olson & Bear, LLP

(57) ABSTRACT

The present invention relates to a method for separating and purifying a lactone compound with an unsaturated alkyl group from a lactone compound with a saturated alkyl group which is an analog thereof. More specifically, the present invention relates to a method for effectively separating a lactone compound with an unsaturated alkyl group such as FK506 at high purity by extraction with a silver ion ($Ag^+$) solution without use of column chromatography.

8 Claims, 2 Drawing Sheets

[Figure 1]
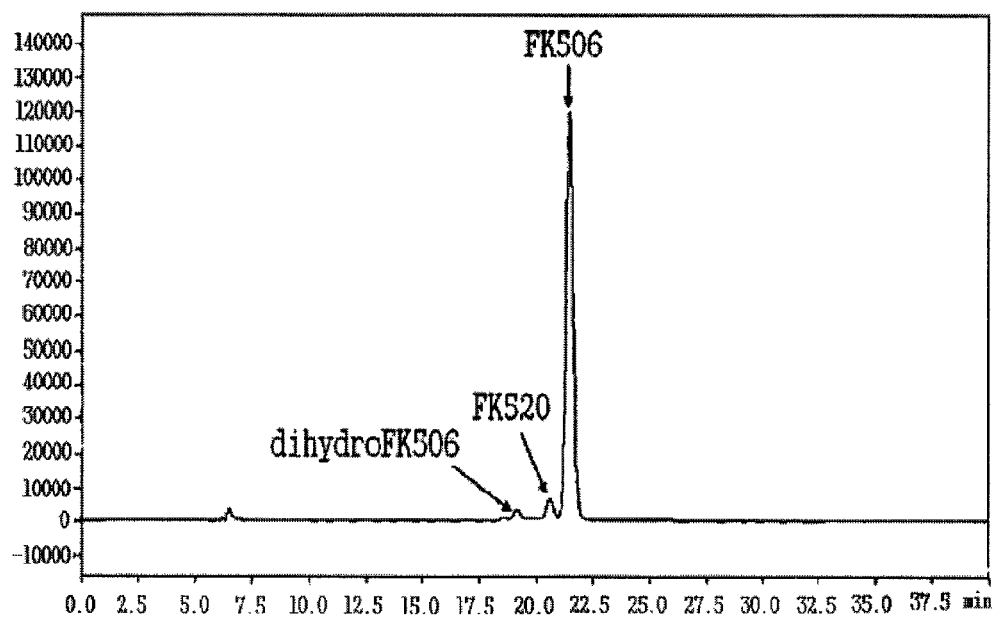

[Figure 2]
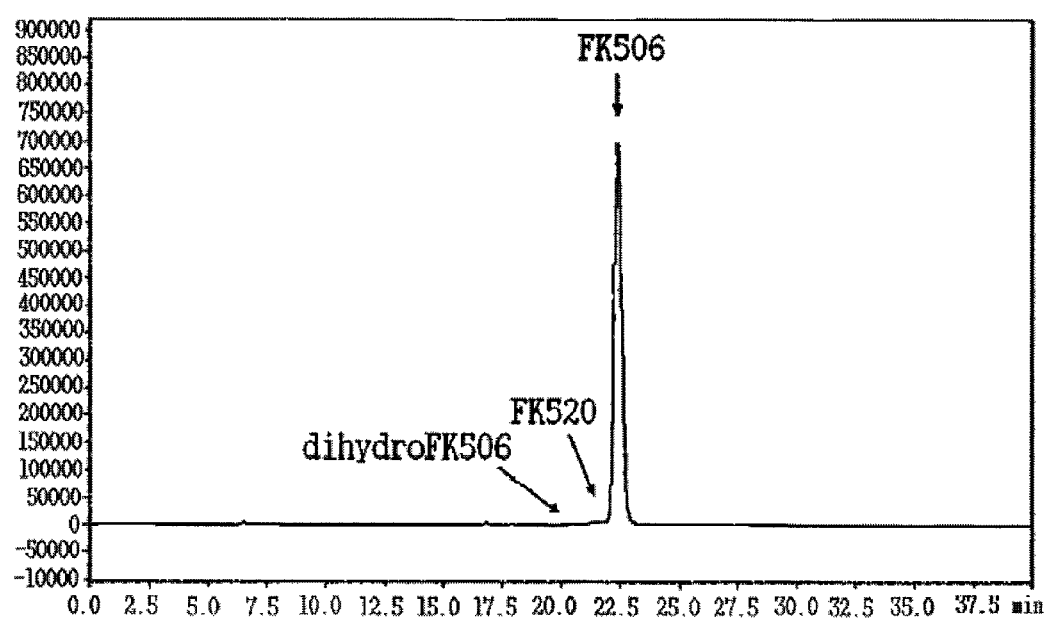

PURIFICATION METHOD OF LACTONE COMPOUNDS CONTAINING UNSATURATED ALKYL GROUP BY EXTRACTION WITH SILVER ION SOLUTION

CROSS-REFERENCE TO RELATED APPLICATIONS

This application is a continuation application under 35 U.S.C. §365(c) of International Application No. PCT/KR2009/004325, filed Aug. 3, 2009 designating the United States. The International Application No. PCT/KR2009/004325 was published in English as WO2010/032919 A1 on Mar. 25, 2010. This application further claims the benefit of the earlier filing date under 35 U.S.C. §365(b) of Korean Patent Application No. 10-2008-0091523 filed Sep. 18, 2008. This application incorporates herein by reference the International Application No. PCT/KR2009/004325 including the International Publication No. WO2010/032919 A1 and the Korean Patent Application No. 10-2008-0091523 in their entirety.

BACKGROUND

1. Field

The present disclosure relates to a method for separating a lactone compound having an unsaturated alkyl group, particularly FK506, and lactone compounds having a saturated alkyl group, particularly FK520 and dihydroFK506, as analogs of the lactone compound having an unsaturated alkyl group using a silver ion ($Ag^+$) solution, thereby eliminating the need for column chromatography.

2. Description of the Related Art

FK506 is a tricyclic macrolide lactone compound that is produced by fermentation of *Streptomyces* species and has immunosuppressive activities. FK506 is used for the prevention of organ transplant rejection and Rh hemolytic diseases of the newborns and the treatment of autoimmune diseases and infectious diseases, etc. FK506 was first reported in 1987 (*J. Antibiotics*, 16, No. 9, 1249-1255, 1987) and is commercially available from Astellas Pharma. Inc. Since FK506 was first developed, various methods for the separation and purification of FK506 have been proposed in many papers and patents.

Fermentation products obtained by the culture of microorganisms typically contain culture media and a variety of metabolites in the culture solutions. For example, an FK506 fermentation product contains structural analogs of FK506 such as FK520 and dihydroFK506. It is known that FK506 and its structural analogs are mostly produced by microorganisms, particularly microorganisms belonging to *Actinomycetes*. FK506 was reported to be produced from strains such as *Streptomyces tsukubaensis* No. 9993, *Streptomyces* sp. ATCC55098, *Streptomyces* sp. ATCC53770 and *Streptomyces* sp. BICC7522 (Muramatsu, H., S. I. Mokhtar, M. Katsuoka and M. Ezaki. 2005, U.S. Pat. No. 4,894,366 and PCT International Publication No. WO 05/098011). FK520 as a structural analog of FK506 also exhibits immunosuppressive activities and antifungal activities and was reported to be produced from *Streptomyces hygroscopicus* subsp. *ascomyceticus* ATCC14891, *Streptomyces hygroscopicus* subsp. *yakusimaensis* 7238, *Streptomyces tsukubaensis* 9993, and other species. A fermentation product of an FK506 producing strain contains FK520 and many structures analogous to FK506. It is very important to remove the analogs (e.g., FK520) of FK506 from the fermentation product for the production of high-quality FK506 for medicinal applications.

Under such circumstances, efforts have been made in industrial fields to find methods for removing FK520 and dihydroFK506 to obtain high-purity FK506. These purification techniques are commonly based on column chromatography. It is widely known that silver ion ($Ag^+$) column chromatography is usually used to separate cis- and trans-isomers of unsaturated fatty acids having the same number of carbon atoms (*J. chromatography* 149 (1978) 417). Silver ion column chromatographic methods for the production of high-purity FK506 are broadly classified into two groups of methods according to the techniques employed: (i) methods using resins pretreated with silver ions (U.S. Pat. No. 6,492,513, U.S. Patent Publication No. 08/000,0834 and PCT International Publication No. WO 05/054253); and (ii) methods for separating a target compound and other compounds by adsorbing a mixture of the compounds to a resin and eluting with a solvent containing silver ions (see U.S. Pat. Nos. 6,576, 135 and 6,881,341).

More specifically, U.S. Pat. No. 6,492,513 discloses a method for separating high molecular weight compounds (such as FK506 and FK520) from each other using a sulfonic acid group-containing cation-exchange resin pretreated with silver ions, for example, silver ions provided from silver nitrate.

Further, U.S. Patent Publication No. 08/000,0834 describes a process for the chromatographic separation of FK506 using a silver modified sorbent selected from the group consisting of silver modified aluminum oxide, zirconium oxide, styrene divinylbenzene copolymer, adsorption resin, cation-exchange resin, anion-exchange resin, reverse phase silica gel and cyano silica gel.

Further, PCT International Publication No. WO 05/054253 discloses a process for purifying FK506 including transferring FK506 to an organic solvent using a solvent for layer separation, treating the organic layer with ammonia gas to phase out impurities, and optionally repeating reverse phase chromatography.

The use of expensive resins and silver ions and large amounts of organic solvents in the above-mentioned FK506 purification methods incurs high costs, which are economically disadvantageous. Other problems of the purification methods are much time consumed to perform column chromatography and low purification yields.

U.S. Pat. No. 6,576,135 discloses a method for separating FK506 from a mixture of lactone-containing high molecular weight compounds having one or more alkenyl and alkoxy side chains, the method including adsorbing the mixture to a nonionic adsorption resin and eluting with a solvent containing silver ions, or the method including adsorbing the mixture to active alumina and eluting to remove impurities analogous to FK506 from the lactone-containing high molecular weight compounds.

Although these methods are advantageous in that FK520 and dihydroFK506 can be separated to a large extent from FK506, the use of the high priced resin and a large amount of the silver ion-containing organic solvent causes considerable costs and the removal of silver ions and nitric acid present in the resin is both costly and time consuming, which are economically undesirable.

The foregoing discussion in the background section is to provide general background information, and does not constitute an admission of prior art.

SUMMARY

One aspect of the invention provides a method of separating a lactone compound from a mixture. The method may comprise providing a mixture, which comprises a target lactone compound comprising an unsaturated alkyl group, and one or more other lactone compounds comprising a saturated alkyl group; dissolving the mixture in a first organic solvent to prepare a solution of the lactone compounds, wherein the first organic solvent is a water-miscible organic solvent; adding a second organic solvent, which is substantially incapable of dissolving the target lactone compound and is substantially immiscible with water, to the solution of the lactone compounds to prepare a first mixed solution; adding an aqueous silver ion (Ag+) solution to the first mixed solution so that the target lactone compound dissolves into to the aqueous silver ion solution; separating at least part of the aqueous silver ion solution containing the target lactone compound from the first and second organic solvents and collecting the aqueous silver ion solution; adding a third organic solvent, which is water-immiscible and capable of dissolving the target lactone compound, to the separated aqueous silver ion solution to form a second mixed solution containing the target lactone compound; and removing the silver ions from the second mixture to collect the target lactone compound.

According to some embodiments, the target lactone compound in the method may be FK506.

According to some other embodiments, the first organic solvent in the method may be selected from the group consisting of alcohols, ketones, dielectric aprotic organic solvents, and mixtures thereof.

According to still some other embodiments, the first organic solvent in the method may be selected from the group consisting of methanol, ethanol, isopropyl alcohol, acetone, acetonitrile, and mixtures thereof.

According to still some other embodiments, the silver ions in the method may be provided from at least one silver salt selected from the group consisting of silver nitrate (AgNO3), silver acetate (AgCH3COO) and silver sulfate (AgSO4).

According to still some other embodiments, the second organic solvent in the method may be selected from the group consisting of benzene, toluene, hexane, heptane, butanol, chloroform, and mixtures thereof.

According to still some other embodiments, the third organic solvent in the method may be selected from the group consisting of dichloromethane, ethyl acetate, isobutyl acetate, n-butyl acetate, t-butyl acetate, and mixtures thereof.

According to still some other embodiments, said removing the silver ions in the method may comprise adding an aqueous solution of NaCl to the second mixture, thereby precipitating the silver ions.

According to still some other embodiments, the precipitated silver ions in the method may be collected and used to prepare the aqueous silver ion solution for the same method.

BRIEF DESCRIPTION OF THE DRAWINGS

FIG. 1 shows diol-HPLC analysis results of a lactone sample containing FK506 and its analogs.

FIG. 2 shows HPLC analysis results of a sample purified by a method according to some embodiments of the present invention.

DETAILED DESCRIPTION OF EMBODIMENTS

It is suggested that a lactone compound having an unsaturated alkyl group capable of bonding to a silver ion and lactone compounds having a saturated alkyl group not capable of bonding to a silver ion despite having the same skeleton structure will exhibit different physical properties in a silver ion solution (particularly differences in solubility and crystallization in the solvent). Accordingly, one aspect of the present invention is to provide an efficient method for separating a lactone compound having an unsaturated alkyl group capable of bonding to a silver ion and lactone compounds having a saturated alkyl group not capable of bonding to a silver ion without the need for column chromatography using an expensive resin to separate the two kinds of compounds.

Since FK506 is a medicinal agent useful for the treatment of autoimmune diseases, organ transplant rejection, Rh hemolytic diseases of the newborns, etc., the presence of impurities would be undesirable. Governmental agencies regulate allowable levels of impurities in drugs. Therefore, a need for methods for reducing the level of impurities in drugs and the commercial value thereof are obvious.

As a result of intensive research, the present inventors have developed a simple and efficient method for separating a lactone compound having an unsaturated alkyl group capable of bonding to a silver ion and lactone compounds having a saturated alkyl group not capable of bonding to a silver ion despite having the same skeleton structure by using a silver ion solution instead of column chromatography using a high priced resin, based on the prediction that the two kinds of lactone compounds will exhibit different physical properties in the silver ion solution, particularly differences in solubility and crystallization in the solvent.

The present inventors have also developed a method for selectively extracting and separating a lactone compound having an unsaturated alkyl group and lactone compounds having a saturated alkyl group from the mixture thereof by using a solvent containing silver ions. One aspect of the present invention is that the lactone compound (e.g., FK506) having an unsaturated alkyl group, which has a high affinity for silver ions, is present in the silver ion solution and its analogs (e.g., FK520, dihydroFK506, everolimus, pimecrolimus and rapamycin) having no affinity for silver ions are present in a solvent layer containing no silver ions and having a higher solubility parameter. The method according to some embodiments of the present invention includes recovering high-purity FK506 from the silver ion solution.

The method according to certain embodiments of the present invention is industrially applicable in an easy manner because it does not use column chromatography. In addition, some embodiments of the present invention enable purification of the lactone compound having an unsaturated alkyl group despite the use of small amounts of solvents. Furthermore, according to some embodiments of the present invention, there are advantages of reusability of the silver ion solution, which is favorable in terms of cost effectiveness, and simple processing. Moreover, according to some embodiments of the present invention, purification time and cost can be markedly reduced and the production yield of the target compound (e.g., FK506) can be increased.

Some embodiments of the present invention provide a method for effectively separating a lactone compound having an unsaturated alkyl group and lactone compounds having a saturated alkyl group as structural analogs of the lactone compound having an unsaturated alkyl group without the need for chromatography using an expensive resin. Specifically, according to some embodiments of the present invention, a lactone compound having an unsaturated alkyl group, particularly FK506, is separated and purified from its analogs such as FK520 and dihydroFK506, which are similar to the lactone compound having an unsaturated alkyl group in terms of molecular weight, structure and physical properties, in a simple way without structural modification of the lactone compounds.

Some embodiments of the present invention provide a method for purifying a lactone compound having an unsaturated alkyl group, the method including:

dissolving a mixture of a lactone compound having an unsaturated alkyl group and lactone compounds having a saturated alkyl group in a water-miscible organic solvent to prepare a solution of the lactone compounds (first step);

adding an organic solvent hardly dissolving the lactone compound having an unsaturated alkyl group and poorly miscible with water to the solution of the lactone compounds (second step);

adding an aqueous silver ion ($Ag^+$) solution to the mixed solution of the second step to allow the lactone compound having an unsaturated alkyl group to migrate to the aqueous silver ion solution (third step);

separating the aqueous silver ion solution containing the lactone compound having an unsaturated alkyl group and the organic solvent layer and collecting the aqueous silver ion solution (fourth step);

adding a water-immiscible organic solvent capable of dissolving the lactone compound having an unsaturated alkyl group present in the aqueous silver ion solution to the aqueous silver ion solution to extract the lactone compound having an unsaturated alkyl group (fifth step); and removing the silver ions present in the extracted lactone compound having an unsaturated alkyl group and collecting the lactone compound having an unsaturated alkyl group as a crystal (sixth step).

The lactone compound having an unsaturated alkyl group may be FK506. The lactone compounds having a saturated alkyl group may be selected from the group consisting of FK520, dihydroFK506, everolimus, pimecrolimus, rapamycin, and mixtures thereof.

The water-miscible organic solvent used in the first step may be selected from the group consisting of alcohols, ketones, dielectric aprotic organic solvents, and mixtures thereof.

The water-miscible organic solvent used in the first step may be selected from the group consisting of methanol, ethanol, isopropyl alcohol, acetone, acetonitrile, and mixtures thereof.

The silver ions used in the third step may be provided from at least one silver salt selected from the group consisting of silver nitrate ($AgNO_3$), silver acetate ($AgCH_3COO$) and silver sulfate ($AgSO_4$).

The solvent hardly dissolving the lactone compound having an unsaturated alkyl group and poorly miscible with water used in the second step may be selected from the group consisting of hydrocarbons, heterocyclic compounds, ethers, esters, and mixtures thereof. The solvent used in the second step is preferably selected from the group consisting of benzene, toluene, hexane, heptane, butanol, chloroform, and mixtures thereof.

The water-immiscible organic solvent used in the fifth step to dissolve the lactone compound having an unsaturated alkyl group present in the aqueous silver ion solution may be selected from the group consisting of hydrocarbons, heterocyclic compounds, ethers and esters. The organic solvent used in the fifth step is preferably selected from the group consisting of dichloromethane, ethyl acetate, isobutyl acetate, n-butyl acetate, t-butyl acetate, and mixtures thereof.

In the sixth step, the silver ions may be removed using an aqueous solution of NaCl.

The silver ion solution remaining after purification may be reused.

Specifically, the method according to some embodiments of the present invention is carried out by the following procedure. First, a mixture of a lactone compound having an unsaturated alkyl group and lactone compounds having a saturated alkyl group is dissolved in a water-miscible organic solvent, and a solvent hardly miscible with an appropriate amount of water is added thereto. Subsequently, an aqueous solution containing silver ions is added to selectively extract the lactone compound having an unsaturated alkyl group having an affinity for the silver ions. Thereafter, the aqueous silver ion solution containing the lactone compound having an unsaturated alkyl group is collected, and then the lactone compound having an unsaturated alkyl group is extracted with an organic solvent capable of dissolving the lactone compound. Finally, the silver ions are removed, followed by crystallization to obtain the high-purity product.

The individual steps of the method according to some embodiments of the present invention will now be described in detail. The lactone compounds used in some embodiments may be a monocyclic, bicyclic or tricyclic ring system. Examples of monocyclic lactone compounds include erythromycin, leucomycin and methymycin. Examples of tricyclic lactone compounds include substances having the structures mentioned in U.S. Pat. Nos. 5,624,842 and 4,894,366 (see Formula 1), rapamycin, and rapamycin derivatives.

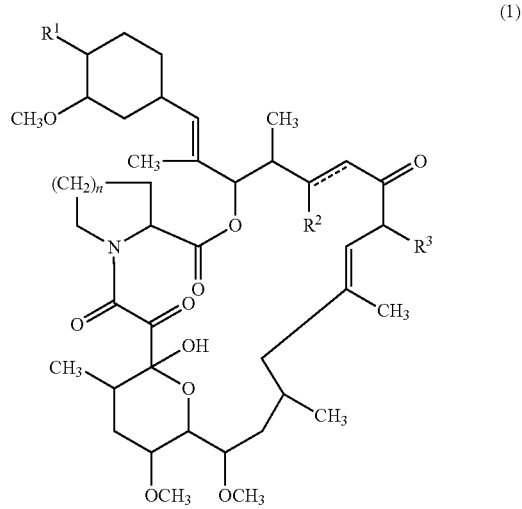

(1)

wherein $R^1$ is a hydroxyl group, a 1-(lower alkylthio)(-lower) alkyloxy group, a tri(lower)alkylsilyloxy group, a lower alkyl-diphenylsilyloxy group or a pharmaceutically acceptable protected hydroxyl group selected from pharmaceutically acceptable organic carboxylic acyloxy groups and pharmaceutically acceptable organic sulfonic acyloxy groups, $R^2$ is hydrogen, a hydroxyl group or a lower alkenoyloxy group, $R^3$ is a methyl, ethyl, propyl or allyl group, n is 1 or 2, and the solid and dashed lines represent a single or double bond, provided that when each $R^1$ and $R^2$ is a hydroxyl group, n is 2 and the solid and dashed lines represent a single bond, $R^3$ is methyl, propyl or allyl or a pharmaceutically acceptable basic salt thereof.

Alternatively, $R^1$ is a hydroxyl group, a lower alkylthioalkoxy group, a tri(lower)alkylsilyloxy group, a lower alkyl-diphenylsilyloxy group, a lower alkenoyloxy group optionally substituted with a carboxyl group, a lower cycloalkoxy (lower)alkenoyloxy group optionally substituted with two lower alkyl groups on the lower cycloalkyl moiety, a camphorsulfonyloxy group, an aroyloxy group optionally substituted with one or more nitro groups where the aroyl moiety is selected from the group consisting of benzoyl, toluoyl, xyloyl and naphthoyl, an arenesulfonyloxy group optionally substituted with a halogen where the arene moiety is selected from the group consisting of benzene, toluene, xylene and naphthalene, or a phenyl(lower)alkenoyloxy group optionally substituted with lower alkoxy and trihalo(lower)alkyl groups, $R^2$ is hydrogen, a hydroxyl group or a lower alkenoyloxy group, $R^3$ is a methyl, ethyl, propyl or allyl group, n is 1 or 2, and the solid and dashed lines represent a single or double bond, provided that when each $R^1$ and $R^2$ is a hydroxyl group, n is 2 and the solid and dashed lines represent a single bond, $R^3$ is methyl, propyl or allyl or a pharmaceutically acceptable basic salt thereof.

The tricyclic lactone compounds may be those represented by Formula 2:

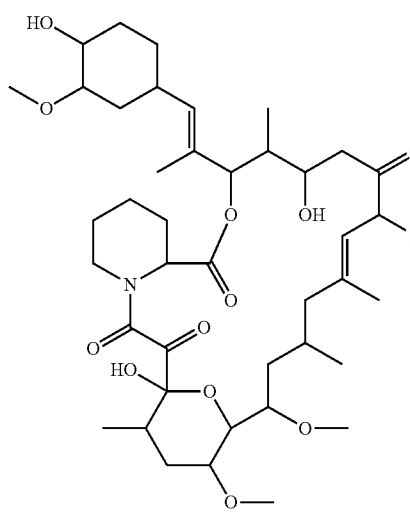

(2)

wherein R is a methyl (FK523), ethyl (FK520), propyl (dihydroFK506) or allyl group (FK506).

The unsaturated alkyl group of the lactone compound is especially a lower alkenyl group such as vinyl, propenyl (allyl or 1-propenyl), butenyl, isobutenyl, pentenyl or hexenyl, more preferably vinyl or propenyl. The saturated alkyl groups of the lactone compounds are methyl, ethyl, propyl, butyl, isobutyl, pentyl and hexyl groups, more preferentially ethyl and propyl groups.

The water-miscible solvent capable of dissolving the lactone compounds may be an alcohol, a ketone or a dielectric aprotic solvent. The solvent is preferably selected from methanol, ethanol, isopropyl alcohol, acetone, acetonitrile and mixtures thereof.

The solvent hardly dissolving the lactone compound having an unsaturated alkyl group and poorly miscible with water may be selected from hydrocarbons, heterocyclic compounds, ethers, esters, and mixtures thereof. The solvent is preferably selected from the group consisting of benzene, toluene, hexane, heptane, butanol, chloroform and mixtures thereof.

In the first step, the concentrations of the lactone compounds dissolved in the solvent may be varied. For example, the concentrations of FK506 and its structural analogs as the lactone compounds are in the range of 1 to 200 g/l and preferably 25 to 150 g/l of the water-miscible organic solvent. Acetone is preferred as the solvent. If the solution of the lactone compounds has a low concentration, the amount of silver ions necessary to purify FK506 is relatively increased, which is uneconomical. Meanwhile, if the solution of the lactone compounds has a high concentration, the addition of water leads to the formation of excessive crystal, making selective crystallization difficult.

In the second step, the amount of the solvent poorly miscible with water and hardly dissolving the desired lactone compound may be appropriately adjusted depending on the kind of the water-miscible organic solvent and whether the lactone compounds are precipitated. The volume of the solvent may be 1 to 100 times greater than that of the water-miscible organic solvent. For example, in the case of the lactone compound FK506 and its analogs, hexane as the water-immiscible solvent is preferably used in an amount 5 to 20 times greater than acetone as the water-miscible solvent.

The aqueous silver ion solution used in the third step may be a 0.5 to 10 M aqueous solution of a silver salt such as silver nitrate capable of providing silver ions. The concentration of the aqueous silver ion solution is preferably in the range of 1 to 5 M. The mixed solution of the second step is treated with the silver ion solution in the temperature range of −10 to 50° C. for 0.5 to 24 hr, which is a time for sufficient mixing. Preferably, FK506 and its analogs are treated with the silver ion solution at 10 to 40° C. for 1 to 12 hr. After the aqueous silver ion solution layer is collected, a water-miscible solvent capable of dissolving the lactone may be added in an appropriate amount to repeatedly recover the aqueous silver ion solution. The number of the repetitions and the amount of the solvent used may be varied depending on the content of impurities in the final product.

The silver ion solution can be reused. An organic solvent suitable for reuse, i.e. a water-immiscible organic solvent capable of dissolving the lactone compound having an unsaturated alkyl group, can be used to separate the lactone compound. For example, after FK506 present in the aqueous silver ion solution layer is extracted with ethyl acetate, the aqueous silver ion solution is separated and collected from the ethyl acetate layer. The collected aqueous silver ion solution can be reused.

The lactone compounds having an alkyl group can be obtained by fermentation of microorganisms. Alternatively, the lactone compounds having an alkyl group may also be provided by artificial synthesis. In some embodiments of the present invention, FK506 is used as the lactone compound having an unsaturated alkyl group and structural analogs of FK506, such as FK520 and dihydroFK506, are used as the lactone compounds having a saturated alkyl group. These lactone compounds are produced by fermentation of microorganisms.

Increases in the concentration of silver ions in the aqueous silver ion solution, the amount of the aqueous silver ion solution, the number of extractions with the aqueous silver ion solution, the amount of the solvent poorly miscible with water and hardly dissolving FK506 and the number of treatments with the solvent poorly miscible with water and hardly dissolving FK506 lead to an increase in the purity of FK506 and a relative decrease in the proportions of FK520 and dihydroFK506. As the concentration of the silver ions increases or the amount of the water-immiscible solvent hardly dissolving FK506 decreases, the recovery rate of FK506 increases.

Hereinafter, some embodiments of the present invention will be explained in more detail with reference to the following examples. However, it will be apparent to those skilled in the art that these examples are not meant in any way to restrict the scope of the invention.

EXAMPLES

Example 1

Preparation of Sample

In this example, a mixture of lactone compounds having an alkyl side chain, particularly FK506, FK520 and dihydroFK506, was prepared. First, 20 ml of a pre-culture medium containing oxidized starch (0.3 g), glycerin (0.21 g), meat peptone (0.09 g), yeast extract (0.09 g), soy peptone (0.15 g) and AZ-20R (0.015 ml) was placed in a 500 ml flat-bottom Erlenmeyer flask, followed by sterilization. The genus *Streptomyces* strain GT 1005 was inoculated into the sterilized medium and cultured at 27-30° C. and 240 rpm for 36 hr. 2 L of a first seed culture medium containing oxidized starch (20 g), glycerin (20 g), fresh soybean flour (10 g), calcium carbonate (4 g), CSL (45%, 10 ml) and AZ-20R (1 ml, pH 6.5) was placed in a 5 L flat-bottom Erlenmeyer flask, followed by sterilization. 10 ml of the pre-culture solution was inoculated into the sterilized culture medium and cultured at 27-30° C. for 36 hr. 300 L of a second seed culture medium containing oxidized starch (6 kg), glycerin (3 kg), fresh soybean flour (1.5 kg), yeast extract (0.6 kg), calcium carbonate (0.6 kg), 45% CSL (1.5 L) and AZ-20R (0.3 kg) was sterilized, inoculated with 2 L of the first seed culture solution, and cultured at a temperature of 27-30° C. and an aeration rate of 0.5-1 VVM for 24 hr while agitating at a rate of 50-300 rpm. 2.7 kl of a main culture medium containing oxidized starch (210 kg), fresh soybean flour (15 kg), yeast flour (51 kg), calcium carbonate (3 kg), ammonium sulfate (3 kg) and AZ-20R (6 L) was prepared in a 5 kl fermentation tank. Caustic soda was added to the tank to adjust the pH of the main culture medium to 8.5, followed by sterilization. 150 L of HP-20 as an adsorption resin was hydrated with water until the final volume reached 300 L, followed by sterilization. The total amount of the second seed culture solution was aseptically inoculated into a mixture of the sterilized medium and the sterilized adsorption resin and cultured at a temperature of 27-30° C. and an aeration rate of 0.5-1 VVM for 6 days while agitating at a rate of 50-200 rpm.

Example 2

Preparation of Lactone Sample

The HP20 resin (150 L) was recovered from the culture solution through a Nutsche filter and washed with water. The resin was extracted with 500 L of acetone to obtain an extract containing FK506, FK520, dihydroFK506, etc. A mixture of water and the extract in the same volume ratio was adsorbed to a column packed with 200 L of a resin (HP20) at a flow rate of 2 RV (resin volume)/hr and 75% acetone was passed at a rate of 1 RV/hr through the column. 3 RV was eluted. HPLC analysis results of the eluate show the presence of 873.6 g of FK506 in a purity of 62%. Excess NaCl was added to the eluate to separate the water layer and the acetone layer from each other. The supernatant was collected and concentrated under reduced pressure. The concentrate was dissolved in a mixed solvent of acetone, hexane and triethylamine (20:80: 0.5) and adsorbed to silica gel (30 kg) filled with the same mixed solvent. After the silica gel was washed with 100 L of the same mixed solvent at a flow rate of 1 RV/hr, 200 L of a mixed solvent of acetone, hexane and triethylamine (30:70: 0.5) and 100 L of a mixed solvent of acetone, hexane and triethylamine (40:60:0.5) were passed at rates of 1 RV/hr through the silica gel. The obtained eluates were analyzed by HPLC. The FK506-containing eluates were collected and concentrated at 50° C. under reduced pressure. The concentrate was dissolved in 80 L of acetone and 240 L of water was added thereto. Crystallization was performed at 4° C. for 12 hr. The crystal was filtered through a filter cloth and dried in a vacuum dryer at 45° C. for 6 hr. The purity of FK506 in the dried crystal (453.7 g) was 87.2%. 100 g of the crystal was dissolved in 1 L of ethyl acetate and 20 g of activated charcoal was added thereto. The mixture was stirred for 1 hr and filtered through Whatman filter paper No. 2. The filtrate was concentrated under reduced pressure. The concentrate was dissolved in 4 L of acetone and 12 L of water was added thereto. Then, the solution was allowed to stand at 4° C. for 12 hr to form a crystal. The crystal was filtered through a filter cloth and dried in a vacuum dryer at 45° C. for 6 hr to prepare a lactone sample.

Example 3

Analytical Methods

Two analytical methods were used to measure the contents and purities of FK506 and its analogs. The contents of the compounds in an aqueous solution were analyzed by HPLC (column: Hypersil GOLD C18 column (4.6×250 mm), mobile phase: 50% acetonitrile, flow rate: 1 ml/min, column temperature: 55° C., detection wavelength: 210 nm), and the purities of the crystallized final compounds were analyzed using a diol column HPLC (columns: two Supercosil LC-Diol analysis columns (4×250 mm, 5 μm) connected in series, mobile phase: mixed solvent of n-hexane, n-butylchloride and acetonitrile (7:2:1), flow rate: 1 ml/min, detection wavelength: 225 nm). The sample used in the following example was analyzed by C18 column HPLC. As a result, FK506, FK520 and dihydroFK506 were present in amounts of 93.3%, 2.56% and 0.6%, respectively. Diol HPLC analysis results for the sample are shown in FIG. 1. As a result, FK506, FK520 and dihydroFK506 had purities of 92.7%, 4.3% and 2.1%, respectively.

Example 4

Selective Extraction of FK506 with Aqueous Silver Ion Solution

The lactone mixture as the sample was completely dissolved in acetone. After hexane was added to the solution, stirring was continued to sufficiently mix the hexane with the acetone. To the solution was added an aqueous solution of silver nitrate with slow stirring for a certain amount of time. The mixed solution was left standing until a lower layer containing the aqueous silver ion solution and an upper layer containing the hexane were separated from each other. The contents of FK506, FK520 and dihydroFK506 in the lower layer were quantitatively analyzed. For two or more extractions, acetone was further added in an amount corresponding to its original volume to the aqueous silver ion solution layer to compensate for the amount of acetone lost by the hexane treatment. Thereafter, hexane was further added as an extraction solvent. The contents of FK506, FK520 and dihydroFK506 in the aqueous silver ion solution were analyzed by C18 HPLC. The concentration and amount of the sample used, the concentration and amount of the silver ions, the amount of the hexane used and the extraction time were varied according to the experimental conditions shown in Table 1. The obtained results are summarized in Table 1. When extracted with water free of silver ions, the FK520 content was 3.5%, implying that no significant change was observed compared to the FK520 content of the original sample, and the recovery rate was as low as 2.78% (see Test Group 1 in Table 1). In contrast, when extracted with water containing silver ions under the same conditions, the FK520 and dihydroFK506 contents were greatly reduced (see Test Group 2 in Table 1). Impurities such as FK520 and DH-FK506 having an absolute influence on the FK 506 purity were reduced with increasing number of extractions (see Test Groups 3 and 4 in Table 1) or increasing extraction time (see Test Groups 14, 15, 16, 17 and 18 in Table 1). However, when comparing with the test group extracted for 3 hr, there was no significant change in the content ratio of the three main tricyclic compounds in the groups extracted for more than 3 hr. For higher FK506 recovery rate, changes in yield were examined according to increases in the concentration of silver ions, concentration of the sample, the amount of hexane used and the amount of the aqueous silver ion solution. As a result, the recovery rate was markedly increased with increasing concentration of silver ions (see Test Groups 4, 5, 6, 7, 10 and 11 in Table 1). Further, an increase in the concentration of the sample (see Test Groups 4, 8 and 9 in Table 1) and an increase in the amount of the hexane (see Test Groups 4, 5, 6, 7, 11, 12 and 13 in Table 1) led to a reduction in recovery rate. These results suggest that FK506 was optimally extracted with the aqueous silver ion solution when the concentration of the FK506 sample was 28.9-144.8 M, the volume of the hexane was 5-10 times higher than that of the acetone, the concentration of silver ions in the aqueous silver ion solution was 0.9-3.6 M and the volume of the aqueous silver ion solution was about twice that of acetone.

TABLE 1

| | Conditions | | | | | Results | | | | |
|---|---|---|---|---|---|---|---|---|---|---|
| Test Group | FK506 (mg)/ Acetone(ml) FK506 conc. (mM) | Hexane(ml) hexane (ml)/ acetone (ml) | AgNO$_3$ (g)/ Water(ml) AgNO$_3$ conc. (M) | Extraction time (hr) | Number of extractions | FK506/ (FK506 + FK520 + DH − FK506) (%) | FK520/ (FK506 + FK520 + DH − FK506) (%) | DH − FK506/ (FK506 + FK520 + DH − FK506) (%) | FK506 recovery rate (%) | FK506 yield (mg) |
| Sample | — | — | — | — | — | 94.1 | 3.2 | 2.7 | 100 | 814.5 |
| 1 | 814/35 28.9 | 175 5x | 0.65 0.0 | 1.5 | 1 | 96.4 | 3.3 | 0.6 | 2.78 | 22.72 |
| 2 | 814/35 28.9 | 175 5x | 10/65 0.9 | 1.5 | 1 | 99 | 1 | 0.1 | 82.16 | 669.19 |
| 3 | 814/35 28.9 | 175 5x | 10/65 0.9 | 1.5 | 2 | 99.6 | 0.4 | 0 | 69.15 | 563.26 |
| 4 | 814/35 28.9 | 175 5x | 10/65 0.9 | 1.5 | 3 | 100 | 0 | 0 | 50.96 | 415.06 |
| 5 | 814/35 28.9 | 175 5x | 20/65 1.8 | 1.5 | 3 | 100 | 0 | 0 | 80.12 | 652.61 |
| 6 | 814/35 28.9 | 350 10x | 10/65 0.9 | 1.5 | 3 | 100 | 0 | 0 | 32.77 | 266.91 |
| 7 | 814/35 28.9 | 350 10x | 20/65 1.8 | 1.5 | 3 | 100 | 0 | 0 | 61.04 | 497.17 |
| 8 | 1679/35 57.8 | 175 5x | 10/65 0.9 | 1.5 | 3 | 100 | 0 | 0 | 31.74 | 517.03 |
| 9 | 4073/35 144.5 | 175 5x | 10/65 0.9 | 1.5 | 3 | 100 | 0 | 0 | 7.21 | 294.88 |
| 10 | 814/17.5 57.8 | 87.5 5x | 10/32.5 1.8 | 1.5 | 3 | 100 | 0 | 0 | 78.21 | 637.03 |
| 11 | 814/17.5 57.8 | 87.5 5x | 20/33.5 3.6 | 1.5 | 3 | 100 | 0 | 0 | 92.45 | 752.54 |
| 12 | 814/17.5 57.8 | 131.3 7.5x | 20/32.5 3.6 | 1.5 | 3 | 100 | 0 | 0 | 86.86 | 707.5 |
| 13 | 814/17.5 57.8 | 175 10x | 20/32.5 3.6 | 1.5 | 3 | 100 | 0 | 0 | 82.23 | 669.7 |
| 14 | 814/17.5 57.8 | 175 10x | 20/32.5 (3.6) | 1.5 | 1 | 98.6 | 1.3 | 0.1 | 98.74 | 804.204 |
| 15 | 814/17.5 57.8 | 175 10x | 20/32.5 3.6 | 3 | 1 | 99.6 | 0.4 | 0.1 | 96.06 | 782.4 |
| 16 | 814/17.5 (57.8) | 175 10x | 20/32.5 3.6 | 6 | 1 | 99.6 | 0.3 | 0 | 93.75 | 763.6 |

TABLE 1-continued

| Test Group | FK506 (mg)/ Acetone(ml) FK506 conc. (mM) | Hexane(ml) hexane (ml)/ acetone (ml) | AgNO$_3$ (g)/ Water(ml) AgNO$_3$ conc. (M) | Extraction time (hr) | Number of extractions | FK506/ (FK506 + FK520 + DH − FK506) (%) | FK520/ (FK506 + FK520 + DH − FK506) (%) | DH − FK506/ (FK506 + FK520 + DH − FK506) (%) | FK506 recovery rate (%) | FK506 yield (mg) |
|---|---|---|---|---|---|---|---|---|---|---|
| 17 | 814/17.5 57.8 | 175 10x | 20/32.5 3.6 | 9 | 1 | 99.7 | 0.3 | 0 | 95.94 | 748 |
| 18 | 814/17.5 57.8 | 175 10x | 20/32.5 3.6 | 12 | 1 | 99.5 | 0.4 | 0 | 95.94 | 781.4 |

Example 5

Collection of Lactone Compounds from the Silver Ion Solution

The lactone compounds were collected from the aqueous silver ion solution extracted from Test Group 12 of Example 4. Ethyl acetate was added in a volume twice the volume of the aqueous silver ion solution. The resulting solution was strongly mixed for 1 hr. FK506 was recovered from the ethyl acetate layer and concentrated under reduced pressure. To this concentrate was added acetone in the same volume as acetone used in the test group. After the mixture was completely dissolved, a saturated aqueous solution of NaCl was added to precipitate the silver ions in the form of AgCl, strongly mixed with the same volume of ethyl acetate for at least 1 hr, and left standing for layer separation. The ethyl acetate layer was separated and completely concentrated under reduced pressure. The sample was dissolved in acetone and a 4-fold volume of water was slowly added thereto to form a white crystal. Freeze drying afforded 507.3 mg of the crystal. The FK506 purity was 98.6% as determined by diol-HPLC. Any impurity was not present in an amount of 0.5% or more (FIG. 2). The recovery rate of FK506 was 70.7% as calculated from the graph of FIG. 2. The same extraction procedure as above was applied to Test Group 13. As a result, the purity and recovery rate of FK506 in Test Group 13 were 98.5% and 72.3%, respectively.

The method according to some embodiments of the present invention is useful for the purification of lactone compounds (including FK506) having an unsaturated alkyl group. Therefore, some embodiments of the present invention can be used for medicinal applications.

What is claimed is:

1. A method of separating a lactone compound FK506 from a mixture, the method comprising:
   providing a mixture which comprises the lactone compound FK506 and one or more other lactone compounds comprising a saturated alkyl group;
   dissolving the mixture in a first organic solvent to prepare a solution of the lactone compounds, wherein the first organic solvent is a water-miscible organic solvent;
   adding a second organic solvent, which is substantially incapable of dissolving the lactone compound FK506 and is substantially immiscible with water, to the solution of the lactone compounds to prepare a first mixed solution;
   adding an aqueous silver ion (Ag$^+$) solution to the first mixed solution so that the lactone compound FK506 dissolves into to the aqueous silver ion solution;
   separating at least part of the aqueous silver ion solution containing the lactone compound FK506 from the first and second organic solvents and collecting the aqueous silver ion solution;
   adding a third organic solvent, which is water-immiscible and capable of dissolving the lactone compound FK506, to the separated aqueous silver ion solution to form a second mixed solution containing the lactone compound FK506; and
   removing the silver ions from the second mixture to collect the lactone compound FK506.

2. The method of claim 1, wherein the first organic solvent is selected from the group consisting of alcohols, ketones, dielectric aprotic organic solvents, and mixtures thereof.

3. The method of claim 1, wherein the first organic solvent is selected from the group consisting of methanol, ethanol, isopropyl alcohol, acetone, acetonitrile, and mixtures thereof.

4. The method of claim 1, wherein the silver ions are provided from at least one silver salt selected from the group consisting of silver nitrate (AgNO$_3$), silver acetate (AgCH$_3$COO) and silver sulfate (AgSO$_4$).

5. The method of claim 1, wherein the second organic solvent is selected from the group consisting of benzene, toluene, hexane, heptane, butanol, chloroform, and mixtures thereof.

6. The method of claim 1, wherein the third organic solvent is selected from the group consisting of dichloromethane, ethyl acetate, isobutyl acetate, n-butyl acetate, t-buty acetate, and mixtures thereof.

7. The method of claim 1, wherein said removing the silver ions comprises: adding an aqueous solution of NaCl to the second mixture, thereby precipitating the silver ions.

8. The method of claim 1, wherein the precipitated silver ions are collected and used to prepare the aqueous silver ion solution for the same method.

* * * * *